(12) United States Patent
Stahurski

(10) Patent No.: US 6,656,180 B2
(45) Date of Patent: Dec. 2, 2003

(54) APPARATUS FOR RETAINING VERTEBRAE IN A DESIRED SPATIAL RELATIONSHIP

(75) Inventor: Terrance Stahurski, Seven Hills, OH (US)

(73) Assignee: Stahurski Consulting Inc., Seven Hills, OH (US)

( * ) Notice: Subject to any disclaimer, the term of this patent is extended or adjusted under 35 U.S.C. 154(b) by 0 days.

(21) Appl. No.: 09/946,900

(22) Filed: Sep. 5, 2001

(65) Prior Publication Data

US 2003/0045876 A1 Mar. 6, 2003

(51) Int. Cl.$^7$ ............................................... A61B 17/70
(52) U.S. Cl. ..................................................... 606/61
(58) Field of Search ..................................... 606/60, 61

(56) References Cited

U.S. PATENT DOCUMENTS

| | | | |
|---|---|---|---|
| 3,862,631 A | * 1/1975 | Austin | ..................... 606/60 |
| 4,274,401 A | 6/1981 | Miskew | |
| 5,176,678 A | 1/1993 | Tsou | |
| 5,201,734 A | * 4/1993 | Cozad et al. | .................. 606/62 |
| 5,395,370 A | 3/1995 | Muller et al. | |
| 5,476,464 A | 12/1995 | Metz-Stavenhagen et al. | |
| 5,534,002 A | 7/1996 | Brumfield et al. | |
| 5,545,167 A | 8/1996 | Lin | |
| 5,562,662 A | * 10/1996 | Brumfield et al. | ............ 606/61 |
| 5,575,792 A | 11/1996 | Errico et al. | |
| 5,609,593 A | 3/1997 | Errico et al. | |
| 5,609,594 A | 3/1997 | Errico et al. | |
| 6,126,660 A | * 10/2000 | Dietz | ........................... 606/61 |
| 6,352,537 B1 | * 3/2002 | Strnad | .......................... 606/61 |

FOREIGN PATENT DOCUMENTS

| | | | | |
|---|---|---|---|---|
| FR | 2817143 | * | 5/2002 | ............ A61B/17/70 |
| JP | 191614 | * | 7/2002 | ........... A61B/17/58 |

* cited by examiner

*Primary Examiner*—Kevin Shaver
*Assistant Examiner*—Michael B. Priddy
(74) *Attorney, Agent, or Firm*—Tarolli, Sundheim, Covell & Tummino L.L.P.

(57) ABSTRACT

An apparatus (10, 110) for use in retaining vertebrae (V) of a spinal column in a desired spatial relationship includes a longitudinal member (12, 112) having a longitudinal axis (13, 113) extendable along the spinal column. A hook (14, 114) connects the longitudinal member (12, 112) to a vertebra (V) of the spinal column. The hook (14, 114) is connectable with the longitudinal member (12, 112) and engageable with the vertebra (V). The hook (14, 114) has a first portion (16, 116) which extends adjacent a first surface (64, 164) of the vertebra (V) when the hook is connected with the vertebra. A second portion (18, 118) of the hook (14, 114) extends adjacent a second surface (62, 162) of the vertebra (V) when the hook is connected with the vertebra so that the vertebra is received between the first and second portions (14, 114 and 18, 118). The second portion (18, 118) is movable relative to the first portion (14, 114) in a direction transverse to the longitudinal axis (13, 113) of the longitudinal member (12, 112) to adjust a distance between the first portion (14, 114) and the second portion (18, 118).

25 Claims, 1 Drawing Sheet

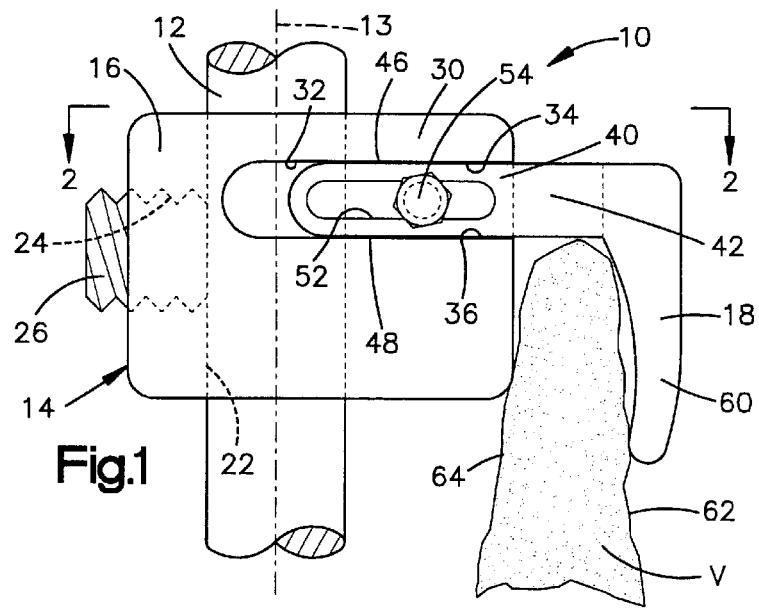
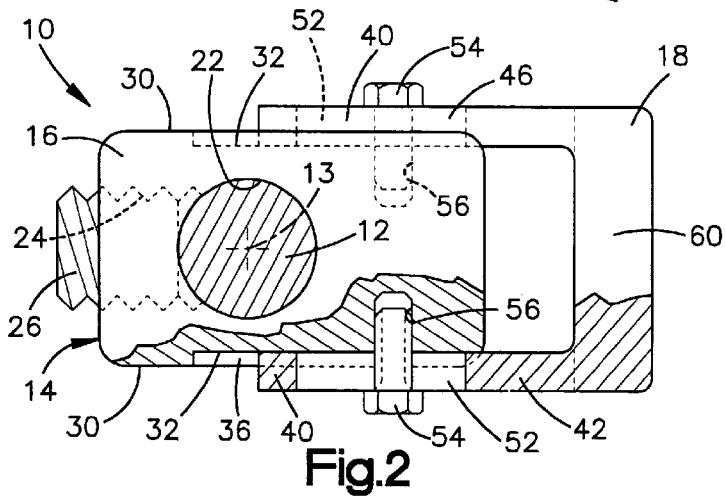
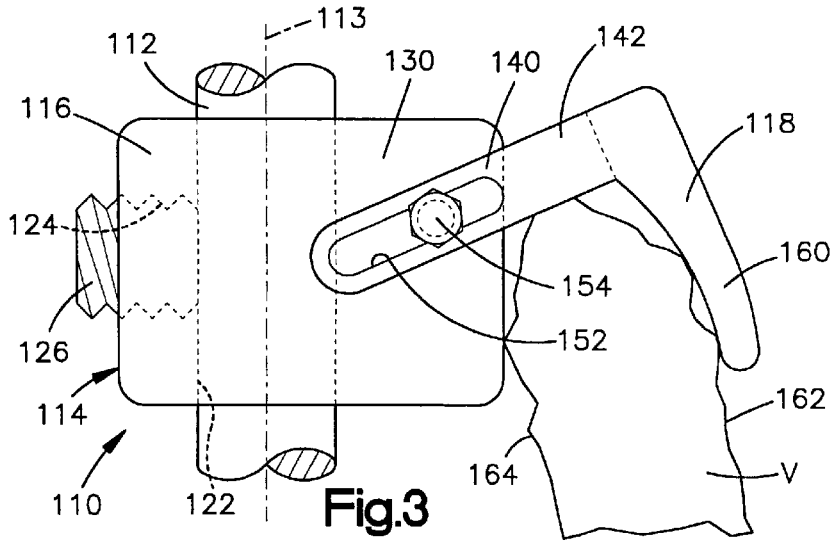

APPARATUS FOR RETAINING VERTEBRAE IN A DESIRED SPATIAL RELATIONSHIP

FIELD OF THE INVENTION

The present invention relates to a spine hook for use in connecting a longitudinal member to a spinal column to retain vertebrae of the spinal column in a desired spatial relationship.

BACKGROUND OF THE INVENTION

Spine hooks have been used to connect longitudinal members or rods to vertebrae of a spinal column to retain the vertebrae in a desired spatial relationship. Each hook has a first portion which extends adjacent a first surface of a vertebra when the hook is connected with the vertebra. A second portion extends adjacent a second surface of the vertebra when the hook is connected with the vertebra so that the vertebra is received between the first and second portions. The distance between the first and second portions is fixed. Accordingly, hooks with various distances between the first and second portions must be provided to connect the longitudinal member to vertebrae having different thicknesses or to connect the longitudinal member to vertebrae spaced from the longitudinal member at different distances.

SUMMARY OF THE INVENTION

An apparatus for use in retaining vertebrae of a spinal column in a desired spatial relationship of the present invention includes a longitudinal member having a longitudinal axis extendable along the spinal column. A hook connects the longitudinal member to a vertebra of the spinal column. The hook is connectable with the longitudinal member and engageable with the vertebra.

The hook has a first portion which extends adjacent a first surface of the vertebra when the hook is connected with the vertebra. A second portion of the hook extends adjacent a second surface of the vertebra when the hook is connected with the vertebra so that the vertebra is received between the first and second portions. The second portion is movable relative to the first portion transverse to the longitudinal axis of the longitudinal member to adjust a distance between the first portion and the second portion. Accordingly, the hook can connect the longitudinal member to vertebrae having different thicknesses or connect the longitudinal member to vertebrae spaced from the longitudinal member at different distances.

BRIEF DESCRIPTION OF THE DRAWINGS

The foregoing and other features of the present invention will become apparent to one skilled in the art to which the present invention relates upon consideration of the following description of the invention with reference to the accompanying drawings, in which:

FIG. 1 is a schematic side view of an apparatus constructed in accordance with a first embodiment of the present invention;

FIG. 2 is an end view of the apparatus, partially in section, taken along the line 2—2 in FIG. 1; and FIG. 3 is a schematic side view of an apparatus constructed in accordance with a second embodiment of the present invention.

DESCRIPTION OF THE INVENTION

The present invention is directed to an apparatus for retaining vertebrae of a spinal column in a desired spatial relationship. FIGS. 1–2 illustrate an apparatus 10 constructed according to a first embodiment of the present invention. The apparatus 10 includes a surgically implantable longitudinal member or rod 12 for maintaining vertebrae V, one of which is shown in FIGS. 1–2, of a spinal column in a desired spatial relationship. The rod 12 has a longitudinal axis 13 and extends along the spinal column. The rod 12 has a length which is at least sufficient to enable the rod to span at least two vertebrae V. Of course, the length of the rod 12 in any particular installation will depend upon the condition to be corrected and the number of vertebrae V to be held in a desired spatial relationship relative to each other by the rod.

The longitudinal member 12 is connected to a vertebra V by a spine hook 14 made of a suitable biocompatible material. The hook 14 has a first or body portion 16 and a second or blade portion 18 extending from the body portion. The blade portion 18 is movable transverse to the longitudinal axis 13 of the rod 12 relative to the body portion 16. The body portion 16 has an opening 22 through which the rod 12 extends. A threaded opening 24 in the body portion 16 intersects the opening 22. A clamping member 26 threadably engages the threaded opening 24 to clamp the rod 12 in the opening 22.

The body portion 16 (FIG. 2) includes opposite sides 30 extending parallel to each other and the longitudinal axis 13 of the rod 12. Each of the sides 30 (FIGS. 1–2) has a groove 32 extending transverse to the longitudinal axis 13 of the rod 12. Each of the grooves 32 (FIG. 1) has side surfaces 34 and 36 extending generally parallel to each other to define the groove 32. A pair of arms 40 of the blade portion 18 are received in the grooves 32 and extend transverse to the axis 13 of the longitudinal member 12. The arms 40 define a connecting portion 42 of the blade portion 18. The arms 40 have parallel surfaces 46 and 48 that engage the parallel surfaces 34 and 36 defining the groove 32. The surfaces 46 and 48 on the arms 40 engage the surfaces 34 and 36 on the body portion 16 to prevent pivoting of the blade portion 18 relative to the body portion.

The arms 40 (FIGS. 1–2) have slots 52 extending transverse to the axis 13 of the longitudinal member 12. Fasteners 54 (FIG. 2) extend through the slots 52 and threadably engage openings 56 in the body portion 16 to connect the blade portion 18 to the body portion. The fasteners 54 clamp the connecting portion 42 to the body portion 16 to prevent movement of the blade portion 18 relative to the body portion. The blade portion 18 is movable transverse to the longitudinal axis 13 of the rod 12 relative to the body portion 16 when the fasteners 54 are not clamping the arms 40 to the body portion.

The blade portion 18 (FIGS. 1 and 2) has an end portion 60 that extends transverse to and between the arms 40. The end portion 60 extends adjacent a first surface 62 of the vertebra V and the body portion 16 extends adjacent a second surface 64 of the vertebra. Accordingly, the vertebra V is received between the end portion 60 and the body portion 16. The end portion 60 moves transverse to the longitudinal axis 13 of the rod 12 relative to the body portion 16 to adjust the distance between the end portion 60 and the body portion 16. It is contemplated that the connecting portion 42 could have markings to show the distance between the end portion 60 and the body portion 16. Accordingly, the hook 14 can receive vertebrae V having different thicknesses. Also, the hook 14 can connect the longitudinal member 12 to vertebrae V spaced from the longitudinal member at different distances.

When the rod 12 is to be connected to the vertebra of the spinal column, the thickness of the vertebra V is measured.

The blade portion 18 is positioned relative to the body portion 16 so that the vertebra V will be received between the end portion 60 and the body portion. Once the blade portion 18 is positioned relative to the body portion 16, the fasteners 54 are tightened to clamp the arms 40 to the body portion 16 and prevent movement of the blade portion 18 relative to the body portion. Once the fasteners 54 are tightened, the hook 14 is placed on the rod 12. The hook 14 is then connected to the vertebra V with the vertebra extending between the end portion 60 and the body portion 16. The clamping member 26 is then threaded into engagement with the rod 12 to clamp the rod to the body portion 16.

An apparatus 110 constructed according to a second embodiment of the present invention is illustrated in FIG. 3. The apparatus 110 includes a surgically implantable longitudinal member or rod 112 having a longitudinal axis 113 for maintaining vertebrae V, one of which is shown in FIG. 3, of a spinal column in a desired spatial relationship. The rod 112 has a length which is at least sufficient to enable the rod to span at least two vertebrae V. Of course, the length of the rod 112 in any particular installation will depend upon the condition to be corrected and the number of vertebrae V to be held in a desired spatial relationship relative to each other by the rod.

The rod 112 is connected to a vertebra V by a spine hook 114 made of a suitable biocompatible material. The hook 114 has a first or body portion 116 and a second or blade portion 118 extending from the body portion. The blade portion 118 is movable transverse to the longitudinal axis 113 of the rod 112 and pivotable relative to the body portion 116. The body portion 116 has an opening 122 through which the rod 112 extends. A threaded opening 124 in the body portion 116 intersects the opening 122. A clamping member 126 threadably engages the opening 124 to clamp the rod 112 to the body portion 116.

The body portion 116 has opposite sides 130, one of which is shown in FIG. 3, extending parallel to the longitudinal axis 113 of the rod 112. A pair of arms 140, one of which is shown in FIG. 3, of the blade portion 118 engage the sides 130 of the body portion 116 and extend transverse to the longitudinal axis 113 of the longitudinal member 112. The arms 140 define a connecting portion 142 of the blade portion 118. The arms 140 have slots 152 extending transverse to the axis 113 of the rod 112. Fasteners 154 extend through the slots 152 and threadably engage openings in the body portion 116 to connect the blade portion 118 to the body portion. The fasteners 154 clamp the arms 140 to the sides 130 of the body portion 116 to prevent movement of the blade portion 118 relative to the body portion. The blade portion 118 is movable relative to the body portion 116 transverse to the axis 113 of the rod 112. The blade portion 118 is also pivotable about the fasteners 154 relative to the body portion 116.

The blade portion 118 has an end portion 160 extending transverse to and between the arms 140. The end portion 160 extends adjacent a surface 162 of the vertebra V and the body portion 116 extends adjacent a surface 164 of the vertebra. Accordingly, the vertebra V is received between the end portion 160 of the blade portion 118 and the body portion 116.

When the rod 12 is to be connected to the vertebra V of the spinal column, the thickness of the vertebra is measured. The blade portion 118 is positioned relative to the body portion 116 by moving the blade portion 118 transverse the longitudinal axis 113 and pivoting the blade portion about the fastener 154. Once the blade portion 118 is positioned relative to the body portion 116, the fasteners 154 are tightened to clamp the arms 140 to the body portion 116 and prevent movement of the blade portion 118 relative to the body portion. After the fasteners 154 are tightened, the hook 114 is placed on the rod 112. The hook 114 is connected with the vertebra V with the vertebra extending between the end portion 160 and the body portion 116. The clamping member 126 is threaded into engagement with the rod 112 to clamp the rod to the body portion 116.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for use in retaining vertebrae of a spinal column in a desired spatial relationship comprising:

a longitudinal member having a longitudinal axis extendable along the spinal column;

a hook connectable with said longitudinal member and engageable with a vertebra of the spinal column, said hook having a first portion which extends adjacent a first surface of the vertebra when said hook is connected with the vertebra and a second portion which extends adjacent a second surface of the vertebra when said hook is connected with the vertebra so that the vertebra is received between said first and second portions, said second portion being movable relative to said first portion transverse to said longitudinal axis of said longitudinal member to adjust a distance between said first portion and said second portion; and a fastener for preventing movement of said second portion relative to said first portion.

2. An apparatus as defined in claim 1 wherein said first portion of said hook is connectable with said longitudinal member and said second portion of said hook extends from said first portion and is engageable with the vertebra.

3. An apparatus as defined in claim 2 wherein said second portion has a connecting portion extending from said first portion transverse to said longitudinal axis of said longitudinal member and an end portion extending from said connecting portion and transverse to said connecting portion, said end portion of said second portion extending adjacent the second surface of the vertebra when said hook is connected with the vertebra.

4. An apparatus as defined in claim 3 wherein said fastener engages said connecting portion to clamp said connecting portion to said first portion and prevent movement of said second portion relative to said first portion.

5. An apparatus as defined in claim 4 wherein said fastener extends through said connecting portion and threadably engages said first portion to clamp said connecting portion to said first portion.

6. An apparatus as defined in claim 5 wherein said connecting portion has a slot extending transverse to said longitudinal axis of said longitudinal member through which said fastener extends.

7. An apparatus as defined in claim 3 wherein said first portion has a groove extending transverse to said longitudinal axis of said longitudinal member into which said connecting portion extends to guide movement of said second portion transverse to said longitudinal axis of said longitudinal member relative to said first portion.

8. An apparatus as defined in claim 7 wherein said first portion has first and second surfaces extending parallel to each other and defining said groove, said first and second surfaces being engageable with first and second surfaces on said connecting portion extending parallel to each other to prevent pivoting of said second portion relative to said first portion.

9. An apparatus as defined in claim 3 wherein said connecting portion includes two arms extending parallel to each other engageable with opposite sides of said first portion, said end portion extending between said arms.

10. An apparatus as defined in claim 1 wherein said first portion has an opening through which said longitudinal member extends.

11. An apparatus as defined in claim 10 further including a clamping member that clamps said longitudinal member to said first portion.

12. An apparatus as defined in claim 1 wherein said second portion is pivotable relative to said first portion.

13. An apparatus as defined in claim 12 wherein said first portion of said hook is connectable with said longitudinal member and said second portion has a connecting portion extending from said first portion transverse to said longitudinal axis of said longitudinal member and an end portion extending transverse to said connection portion, said end portion of said second portion extending adjacent the second surface of the vertebra when said hook is connected with the vertebra.

14. An apparatus as defined in claim 13 wherein said fastener engages said connecting portion to clamp said connecting portion to said first portion and prevent movement of said second portion relative to said first portion, said second portion being pivotable about said fastener relative to said first portion.

15. An apparatus as defined in claim 14 wherein said fastener extends through said connecting portion and threadably engages said first portion to clamp said connecting portion to said first portion.

16. An apparatus as defined in claim 15 wherein said connecting portion has a slot extending transverse to said longitudinal axis of said longitudinal member through which said fastener extends.

17. An apparatus for use in retaining vertebrae of a spinal column in a desired spatial relationship comprising:
   a longitudinal member having a longitudinal axis extendable along the spinal column;
   a hook connectable with said longitudinal member and engageable with a vertebra of the spinal column, said hook having a first portion which extends adjacent a first surface of the vertebra when said hook is connected with the vertebra and a second portion which extends adjacent a second surface of the vertebra when said hook is connected with the vertebra so that the vertebra is received between said first and second portions, said second portion being movable relative to said first portion transverse to said longitudinal axis of said longitudinal member to adjust a distance between said first portion and said second portion, said first portion of said hook being connectable with said longitudinal member and said second portion of said hook extending from said first portion and being engageable with the vertebra, said second portion having a connecting portion extending from said first portion transverse to said longitudinal axis of said longitudinal member and an end portion extending from said connecting portion and transverse to said connecting portion, said end portion of said second portion extending adjacent the second surface of the vertebra when said hook is connected with the vertebra; and
   a fastener engaging said connecting portion to clamp said connecting portion to said first portion and prevent movement of said second portion relative to said first portion.

18. An apparatus as defined in claim 17 wherein said fastener extends through said connecting portion and threadably engages said first portion to clamp said connecting portion to said first portion.

19. An apparatus as defined in claim 18 wherein said connecting portion has a slot extending transverse to said longitudinal axis of said longitudinal member through which said fastener extends.

20. An apparatus for use in retaining vertebrae of a spinal column in a desired spatial relationship comprising:
   a longitudinal member having a longitudinal axis extendable along the spinal column; and
   a hook which connects said longitudinal member to a vertebra of the spinal column, said hook being connectable with said longitudinal member and engageable with the vertebra, said hook having a first portion which extends adjacent a first surface of the vertebra when said hook is connected with the vertebra and a second portion which extends adjacent a second surface of the vertebra when said hook is connected with the vertebra so that the vertebra is received between said first and second portions, said second portion being movable relative to said first portion transverse to said longitudinal axis of said longitudinal member to adjust a distance between said first portion and said second portion, said first portion of said hook being connectable with said longitudinal member and said second portion of said hook extending from said first portion and being engageable with the vertebra, said second portion having a connecting portion extending from said first portion transverse to said longitudinal axis of said longitudinal member and an end portion extending from said connecting portion and transverse to said connecting portion, said end portion of said second portion extending adjacent the second surface of the vertebra when said hook is connected with the vertebra, said first portion having a groove extending transverse to said longitudinal axis of said longitudinal member into which said connecting portion extends to guide movement of said second portion transverse to said longitudinal axis of said longitudinal member relative to said first portion, said first portion having first and second surfaces extending parallel to each other and defining said groove, said first and second surfaces being engageable with first and second surfaces on said connecting portion extending parallel to each other to prevent pivoting of said second portion relative to said first portion.

21. An apparatus for use in retaining vertebrae of a spinal column in a desired spatial relationship comprising:
   a longitudinal member having a longitudinal axis extendable along the spinal column; and
   a hook which connects said longitudinal member to a vertebra of the spinal column, said hook being connectable with said longitudinal member and engageable with the vertebra, said hook having a first portion which extends adjacent a first surface of the vertebra when said hook is connected with the vertebra and a second portion which extends adjacent a second surface of the vertebra when said hook is connected with the vertebra so that the vertebra is received between said first and second portions, said second portion being movable relative to said first portion transverse to said longitudinal axis of said longitudinal member to adjust a distance between said first portion and said second portion, said first portion of said hook being connectable with said longitudinal member and said second portion of said hook extending from said first portion and being engageable with the vertebra, said second portion having a connecting portion extending from said first portion transverse to said longitudinal axis of said longitudinal member and an end portion extending from said connecting portion and transverse to said connecting portion, said end portion of said second portion extending adjacent the second surface of the vertebra when said hook is connected with the vertebra, said connecting portion including two arms extending parallel to each other engageable with opposite sides of said first portion, said end portion extending between said arms.

22. An apparatus for use in retaining vertebrae of a spinal column in a desired spatial relationship comprising:

a longitudinal member having a longitudinal axis extendable along the spinal column;

a hook which connects said longitudinal member to a vertebra of the spinal column, said hook being connectable with said longitudinal member and engageable with the vertebra, said hook having a first portion which extends adjacent a first surface of the vertebra when said hook is connected with the vertebra and a second portion which extends adjacent a second surface of the vertebra when said hook is connected with the vertebra so that the vertebra is received between said first and second portions, said second portion being movable relative to said first portion transverse to said longitudinal axis of said longitudinal member to adjust a distance between said first portion and said second portion, said second portion being pivotable relative to said first portion, said first portion of said hook being connectable with said longitudinal member and said second portion having a connecting portion extending from said first portion transverse to said longitudinal axis of said longitudinal member and an end portion extending transverse to said connecting portion, said end portion of said second portion extending adjacent the second surface of the vertebra when said hook is connected with the vertebra; and a fastener engaging said connecting portion to clamp said connecting portion to said first portion and prevent movement of said second portion relative to said first portion, said second portion being pivotable about said fastener relative to said first portion.

23. An apparatus as defined in claim 22 wherein said fastener extends through said connecting portion and threadably engages said first portion to clamp said connecting portion to said first portion.

24. An apparatus as defined in claim 23 wherein said connecting portion has a slot extending transverse to said longitudinal axis of said longitudinal member through which said fastener extends.

25. An apparatus for use in retaining vertebrae of a spinal column in a desired spatial relationship comprising:

a longitudinal member having a longitudinal axis extendable along the spinal column; and a hook which connects said longitudinal member to a vertebra of the spinal column, said hook being connectable with said longitudinal member and engageable with the vertebra, said hook having a first portion which extends adjacent a first surface of the vertebra when said hook is connected with the vertebra and a second portion which extends adjacent a second surface of the vertebra when said hook is connected with the vertebra so that the vertebra is received between said first and second portions, said second portion being movable relative to said first portion transverse to said longitudinal axis of said longitudinal member to adjust a distance between said first portion and said second portion, said second portion including a connecting portion engageable with said first portion, said entire second portion including said connecting portion being movable relative to said first portion transverse to said longitudinal axis of said longitudinal member.

* * * * *

UNITED STATES PATENT AND TRADEMARK OFFICE
CERTIFICATE OF CORRECTION

PATENT NO. : 6,656,180 B2
DATED : December 2, 2003
INVENTOR(S) : Terrance Stahurski It is certified that error appears in the above-identified patent and that said Letters Patent is hereby corrected as shown below:

Column 6,
Lines 13-14 and 53-54, after "hook" delete "which connects said longitudinal member to a vertebrae of a spinal column, said hook being".
Lines 16 and 56, after "with" delete "the vertebrae" and insert -- a vertebrae of the spinal column --.

Column 7,
Lines 18-19, after "hook" delete "which connects said longitudinal member to a vertebrae of a spinal column, said hook being".
Line 21, after "with" delete "the vertebrae" and insert -- a vertebrae of the spinal column --.

Column 8,
Lines 19-20, after "hook" delete "which connects said longitudinal member to a vertebrae of a spinal column, said hook being".
Line 22, after "with" delete "the vertebrae" and insert -- a vertebrae of the spinal column --.

Signed and Sealed this

Twenty-second Day of June, 2004

JON W. DUDAS
*Acting Director of the United States Patent and Trademark Office*